United States Patent [19]

Handte et al.

[11] Patent Number: 4,668,276
[45] Date of Patent: May 26, 1987

[54] USE OF ARYLOXY COMPOUNDS AS ANTIDOTES

[75] Inventors: Reinhard Handte, Gablingen; Hilmar Mildenberger, Kelkheim; Klaus Bauer, Rodgau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 698,553

[22] Filed: Feb. 6, 1985

[30] Foreign Application Priority Data

Feb. 8, 1984 [DE] Fed. Rep. of Germany ....... 3404401

[51] Int. Cl.$^4$ ...................... A01N 43/76; A01N 37/38
[52] U.S. Cl. ............................................ 71/88; 71/109;
71/108; 71/100; 71/104; 71/116; 71/118;
71/105; 71/103; 71/90; 71/92; 71/94; 71/95;
71/96; 71/98
[58] Field of Search ............................. 71/88, 116, 109

[56] References Cited

U.S. PATENT DOCUMENTS 3,133,810  5/1964  Hamm ..................................... 71/101
3,929,452  12/1975  Kimura et al. ......................... 71/109
4,130,413  12/1978  Handte et al. .......................... 71/88
4,414,020  11/1983  Heier et al. .............................. 71/88
4,416,687  11/1983  D'Amico et al. ...................... 71/109

FOREIGN PATENT DOCUMENTS 3018003  10/1981  Fed. Rep. of Germany .
0053526   5/1975  Japan .
2137092  10/1984  United Kingdom .

OTHER PUBLICATIONS

Weintraub et al., "Formative Activity of Phenoxyacetic Acids," Agricultural and Food Chemistry, vol. 2, No. 19, pp. 996-999 (1954).
Beste et al., "Interaction of EPTC and 2,4-D on Excised Tissue Growth," Weed Science 20(1): pp. 4-7 (1972).

Primary Examiner—Glennon H. Hollrah
Assistant Examiner—P. Morris
Attorney, Agent, or Firm—Curtis, Morris & Safford

[57] ABSTRACT

Compounds of the formula

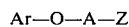

Ar—O—A—Z in which Ar denotes an optionally substituted phenyl-A—CH$_2$— or phenyl-A—CH(CH$_3$)— or naphthyl-A—CH$_2$— or naphthal-A—CH(CH$_3$)— group and Z denotes, inter alia, a carboxyl, (thio)carboxylic ester or carboxamide group, a cyclic imino(thio)ether group or an open or cyclic acetal group, are effective antidotes, in particular for herbicides belonging to the group comprising phenoxyphenoxypropionic acid esters and hetero-aryloxyphenoxypropionic acid esters.

3 Claims, No Drawings

USE OF ARYLOXY COMPOUNDS AS ANTIDOTES

The present invention relates to the use of aryloxy derivatives for protection of crop plants against the harmful side effects of agricultural chemicals.

When plant treatment agents are used, in particular when herbicides are used, undesirable damage can occur to the crop plants which are treated. Particularly when herbicides are applied after the emergence of the crop plants, there is, therefore, often a need to avoid the risk of possible phytotoxicity. Two groups of aryloxy compounds, namely nitriles and amidoximes, have already been suggested for this purpose as so-called "safeners" of "antidotes" (cf. European Pat. No. A 31,938). European Pat. No. A 86,750 describes antidotes which differ from those mentioned only in that they contain a quinoline radical instead of the aryl radical.

It has now been found that the plant-protecting properties of the compounds mentioned in the said applications are not linked to the particular nitrile and amidoxime function; on the contrary, it has been found that the antidote action is also pronounced in the case of aryloxy compounds containing other functional groups.

The present invention therefor relates to the use, as safeners for plant treatment agents, of aryloxy compounds of the formula $$Ar-O-A-Z \qquad (I)$$

in which the individual radicals have the following meanings:

Ar is a phenyl or naphthyl radical each of which can be monosubstituted or disubstituted by identical or different halogen atoms and/or monosubstituted or disubstituted by $CF_3$, $(C_1-C_4)$-alkyl or $(C_1-C_4)$-alkoxy;

A is $-CH_2-$ or $-CH(CH_3)-$,

Z is a radical of the formula

$-COOR^1, -COO-A-COOR^1, -COSR^2, -CON\begin{smallmatrix}R^3\\R^4\end{smallmatrix}$, $-CONCS, -CONHOH,$

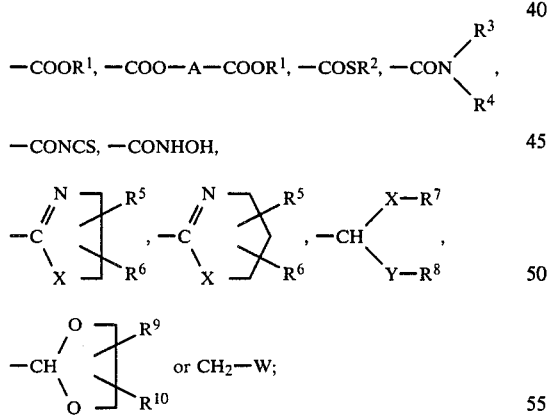

$R^1$ is H; linear or branched $(C_1-C_{12})$-alkyl which is optionally monosubstituted to trisubstituted by fluorine, chlorine or bromine and/or monosubstituted or disubstituted by CN, SCN, OH, $(C_1-C_6)$-alkoxy, $(C_1-C_4)$-alkylthio, $(C_1-C_4)$-alkylsulfinyl, $(C_1-C_4)$-alkylsulfonyl, $(C_1-C_6)$-alkoxy-$(C_2-C_6)$-alkoxy, halogenoalkoxy, methoxyethoxyethoxy, $(C_1-C_4)$-alkylamino, di-$(C_1-C_4)$-alkylamino or $(C_1-C_4)$-alkylcarbonyl, a three-membered to seven-membered, saturated or unsaturated heterocyclic radical which is optionally benzo-condensed and/or substituted by halogen or $(C_1-C_4)$-alkyl and which has up to 3 identical or different heteroatoms (S, O or N), or a phenyl, phenoxy or benzyloxy radical which is optionally monosubstituted or disubstituted by fluorine, chlorine, bromine and/or $(C_1-C_4)$-alkyl; $(C_5-C_6)$-cycloalkyl, $(C_3-C_6)$-alkenyl or $(C_3-C_6)$-alkynyl; phenyl which is optionally monosubstituted or disubstituted by $(C_1-C_4)$-alkyl, $(C_1-C_4)$-alkoxy, halogen or $CF_3$; or the group

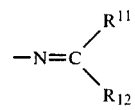

or a cation equivalent of an organic or inorganic base;

$R^2$ is $(C_1-C_6)$-alkyl or $(C_1-C_4)$-alkoxycarbonyl-$(C_1-C_3)$-alkyl;

$R^3$ is H, $(C_1-C_6)$-alkyl, $(C_1-C_4)$-alkoxy, hydroxy-$(C_1-C_4)$-alkyl, $(C_5-C_6)$-cycloalkyl, $(C_3-C_6)$-alkenyl or the group

$R^4$ is H, $(C_1-C_6)$-alkyl, hydroxy-$(C_1-C_4)$-alkyl, cyclopropyl or $(C_3-C_6)$-alkenyl; or phenyl which can be monosubstituted to trisubstituted by $(C_1-C_4)$-alkyl, $(C_1-C_4)$-alkoxy, halogen or $CF_3$; or $R^3$ and $R^4$ together are an alkylene chain having 2, 4 or 5 carbon atoms, in which one $CH_2$ group can optionally be replaced by O, NH or N-$(C_1-C_4)$-alkyl;

$R^5$ and $R^6$ independently of one another are H or $(C_1-C_4)$-alkyl;

X and Y independently of one another are O or S;

$R^7$ and $R^8$ independently of one another are $(C_1-C_6)$-alkyl which can be substituted by halogen, $(C_1-C_4)$-alkoxy or phenyl;

$R^9$ and $R^{10}$ independently of one another are H or $(C_1-C_6)$-alkyl which can be substituted by halogen, OH or $(C_1-C_6)$-alkoxy;

$R^{11}$ is H or $(C_1-C_6)$-alkyl;

$R^{12}$ is $(C_1-C_6)$-alkyl and

W is OH, O-benzyl (optionally substituted by Cl or $CH_3$) or

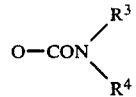

In the above text, "cation equivalents" are to be understood as meaning, in particular, alkali or alkaline earth metal ions and ammonium which is optionally monosubstituted to trisubstituted by lower alkyl or hydroxyalkyl.

Heterocyclic radicals suitable as substitutents of an alkyl group in the $R^1$-position can be, for example: oxiranyl, pyrrolidyl, piperidyl, pyrazolyl, morpholyl, furyl, tetrahydrofuryl, indolyl, azepinyl or triazolyl.

$R^3$ and $R^4$ can, together with the amine nitrogen, preferably form a pyrrolidine, piperidine, morpholine (optionally monosubstituted or disubstituted by $CH_3$) or N-methylpiperazine ring.

The compounds of the general formula I are for the most part known or can be prepared by generally known processes. Some of the compounds are used as herbicides or have been suggested as herbicides (R. Wegler, "Chemie der Pflanzenschutz- und Schädlingsbekämpfungsmittel" ("The Chemistry of Plant Protection Agents and Pest-Combating Agents") II, 274 et seq. including further literature references; U.S. Pat. Nos. 4,062,670 and 4,019,892).

A number of compounds of the general formula I are listed as examples in the tables below.

TABLE I $$\underset{(R^{13})}{\text{Ar}}-O-A-Z$$

| Example | $R^{13}$ | A | Z |
|---|---|---|---|
| 1 | 4-Cl | $CH_2$ | COOH |
| 2 | 4-Cl | $CH_2$ | $COOCH_3$ |
| 3 | 2,4-Di-Cl | $CH_2$ | COOH |
| 4 | 2,4-Di-Cl | $CH_2$ | $COOCH_3$ |
| 5 | 2,4-Di-Cl | $CH_2$ | $COOC_2H_5$ |
| 6 | 2,4-Di-Cl | $CH_2$ | $COOC_3H_7(i)$ |
| 7 | 2,4-Di-Cl | $CH_2$ | $COOC_4H_9(i)$ |
| 8 | 2,4-Di-Cl | $CH_2$ | $COOCH_2CH_2-OCH_3$ |
| 9 | 2,4-Di-Cl | $CH_2$ | $COOC_8H_{17}(i)$ |
| 10 | 2,4-Di-Cl | $CH_2$ | $COSC_2H_5$ |
| 11 | 2,4-Di-Cl | $CH_2$ | $COSC_4H_9$ |
| 12 | 2,4-Di-Cl | $CH_2$ | COONa |
| 13 | 2,4-Di-Cl | $CH_2$ | COOK |
| 14 | 2,4-Di-Cl | $CH_2$ | $COOCH_2-CH_2-OC_4H_9(n)$ |
| 15 | 2,4-Di-Cl | $CH_2$ | $COONH_3C_8H_{17}(i)$ |
| 16 | 2,4-Di-Cl | $CH_2$ | $COONHCH_3(C_8H_{17})_2$ |
| 17 | 2,4-Di-Cl | $CH_2$ | $COONH_2(C_8H_{17}(i))_2$ |
| 18 | 2,4-Di-Cl | $CH_2$ | $COONH(C_8H_{17}(i))_3$ |
| 19 | 2,4-Di-Cl | $CH_2$ | $COONH_2(CH_3)_2$ |
| 20 | 2,4-Di-Cl | $CH_2$ | $COOCH_2CH_2-N\begin{pmatrix}N=\\ \\=N\end{pmatrix}$ |
| 21 | 2,4-Di-Cl | $CH_2$ | $COOCH_2CH_2-N\begin{pmatrix}\\ \\=N\end{pmatrix}$ |
| 22 | 2,4-Di-Cl | $CH_2$ | $COOCH_2-COOCH_3$ |
| 23 | 2,4-Di-Cl | $CH_2$ | $COOCH-\underset{O}{\overset{\|}{C}}-\underset{CH_3}{\overset{\|}{N}}-Ph$ |
| 24 | 2,4-Di-Cl | $CH_2$ | $COOCH(CH_3)-COOCH_3$ |
| 25 | 2,4-Di-Cl | $CH_2$ | $-\overset{O}{\overset{\|}{C}}-NH_2$ |
| 26 | 2,4-Di-Cl | $CH_2$ | $-\overset{O}{\overset{\|}{C}}-NHCH_3$ |
| 27 | 2,4-Di-Cl | $CH_2$ | $-\overset{\|}{\underset{O}{C}}-N(CH_2-CH=CH_2)_2$ |
| 28 | 2,4-Di-Cl, 6-$CH_3$ | $CH_2$ | COOH |
| 29 | 2,4-Di-Cl, 6-$CH_3$ | $CH_2$ | $-COOCH_3$ |
| 30 | 2,4-Di-Cl, 6-$CH_3$ | $CH_2$ | $-COOC_8H_{17}(i)$ |
| 31 | 3,4-Di-Cl | $CH_2$ | COOH |
| 32 | 3,4-Di-Cl | $CH_2$ | $COOCH_3$ |
| 33 | 3,4-Di-Cl | $CH_2$ | $COOC_2H_5$ |
| 34 | 3,4-Di-Cl | $CH_2$ | $COOC_3H_7$ |
| 35 | 3,4-Di-Cl | $CH_2$ | $COOC_4H_9(n)$ |

TABLE I-continued

| Example | R¹³ | A | Z |
|---|---|---|---|
| 36 | 3,4-Di-Cl | CH₂ | COOC₈H₁₇ |
| 37 | 3,4-Di-Cl | CH₂ | COOCH₂—CH₂—O—CH₂—CH₂—O—CH₃ |
| 38 | 3,4-Di-Cl | CH₂ | COOCH₂—CH₂—CH₂—Cl |
| 39 | 3,4-Di-Cl | CH₂ | COOCH₂—CH₂—N(CH₃)₂ |
| 40 | 3,4-Di-Cl | CH₂ | COOCH₂—CH₂—SO₂CH₃ |
| 41 | 3,4-Di-Cl | CH₂ | COOCH₂—CH=CH₂ |
| 42 | 3,4-Di-Cl | CH₂ | COOCH₂—C≡CH |
| 43 | 3,4-Di-Cl | CH₂ | COOCH₂—CH₂—O—C₄H₉ |
| 44 | 3,4-Di-Cl | CH₂ | COOCH₂—COOCH₃ |
| 45 | 3,4-Di-Cl | CH₂ | COOCH₂—COOC₄H₉ |
| 46 | 3,4-Di-Cl | CH₂ | COOCH(CH₃)—COOC₂H₄—OCH₃ |
| 47 | 3,4-Di-Cl | CH₂ | COO—CH₂-(tetrahydrofuran-2-yl) |
| 48 | 3,4-Di-Cl | CH₂ | —COO-cyclohexyl |
| 49 | 3,4-Di-Cl | CH₂ | COOCH₂-phenyl |
| 50 | 3,4-Di-Cl | CH₂ | COO-phenyl |
| 51 | 3,4-Di-Cl | CH₂ | COO—CH₂—C(O)—N(CH₃)₂ |
| 52 | 3,4-Di-Cl | CH₂ | COOCH₂—CH₂—CH(OCH₃)CH₃ |
| 53 | 3,4-Di-Cl | CH₂ | COSC₂H₅ |
| 54 | 3,4-Di-Cl | CH₂ | COSC₄H₉ |
| 55 | 3,4-Di-Cl | CH₂ | COSCH₂—COOCH₃ |
| 56 | 3,4-Di-Cl | CH₂ | COSCH₂-phenyl |
| 57 | 3,4-Di-Cl | CH₂ | COONa |
| 58 | 3,4-Di-Cl | CH₂ | COOK |
| 59 | 3,4-Di-Cl | CH₂ | COONH₃C₃H₇(i) |
| 60 | 3,4-Di-Cl | CH₂ | CONH₂ |
| 61 | 3,4-Di-Cl | CH₂ | CONHCH₃ |
| 62 | 3,4-Di-Cl | CH₂ | CONHC₃H₇(i) |
| 63 | 3,4-Di-Cl | CH₂ | CON(pyrrolidinyl) |
| 64 | 3,4-Di-Cl | CH₂ | —C(O)—N(CH₃)₂ |
| 65 | 3,4-Di-Cl | CH₂ | —C(O)—NH-phenyl |

TABLE I-continued

| Example | R$^{13}$ | A | Z |
|---|---|---|---|
| 66 | 3,4-Di-Cl | CH$_2$ | −C(=O)−N(CH$_3$)−C$_6$H$_5$ |
| 67 | 2,3-Di-Cl | CH$_2$ | COOH |
| 68 | 2,3-Di-Cl | CH$_2$ | COOCH$_3$ |
| 69 | 2,3-Di-Cl | CH$_2$ | COOC$_8$H$_7$ |
| 70 | 3,5-Di-Cl | CH$_2$ | COOH |
| 71 | 3,5-Di-Cl | CH$_2$ | COOCH$_3$ |
| 72 | 3,5-Di-Cl | CH$_2$ | COOC$_2$H$_5$ |
| 73 | 3,5-Di-Cl | CH$_2$ | COOC$_4$H$_9$(n) |
| 74 | 3,5-Di-Cl | CH$_2$ | COOC$_8$H$_{17}$ |
| 75 | 3,5-Di-Cl | CH$_2$ | COOCH$_2$—CH=CH$_2$ |
| 76 | 3,5-Di-Cl | CH$_2$ | COOCH$_2$—CH$_2$—N(CH$_3$)$_2$ |
| 77 | 3,5-Di-Cl | CH$_2$ | COOCH$_2$—C≡CH |
| 78 | 3,5-Di-Cl | CH$_2$ | COSCH$_2$CH$_3$ |
| 79 | 3,5-Di-Cl | CH$_2$ | COS−C$_6$H$_5$ |
| 80 | 3,5-Di-Cl | CH$_2$ | −C(=O)−N(piperidine) |
| 81 | 3,5-Di-Cl | CH$_2$ | −C(=O)−N(H)(C$_2$H$_5$) |
| 82 | 3,5-Di-Cl | CH$_2$ | −C(=O)−N[CH(CH$_3$)$_2$]$_2$ |
| 83 | 3,5-Di-Cl | CH$_2$ | −C(=O)−NHCH$_3$ |
| 84 | 3,5-Di-Cl | CH$_2$ | −C(=O)−N(CH$_3$)$_2$ |
| 85 | 3,5-Di-Cl | CH$_2$ | −C(=O)−NH$_2$ |
| 86 | 3,5-Di-Cl | CH$_2$ | −C(=O)−NHC$_4$H$_9$ |
| 87 | 3,5-Di-Cl | CH$_2$ | −COONa |
| 88 | 3,5-Di-Cl | CH$_2$ | −COOK |
| 89 | 3,5-Di-Cl | CH$_2$ | −COONH$_3$C$_3$H$_7$(i) |
| 90 | 3,5-Di-Cl | CH$_2$ | −COONH(C$_2$H$_4$OH)$_3$ |
| 91 | 3,5-Di-Cl | CH$_2$ | −COONH$_2$(C$_8$H$_{17}$(i))$_2$ |
| 92 | 2,6-Di-Cl | CH$_2$ | COOH |
| 93 | 2,6-Di-Cl | CH$_2$ | COOCH$_3$ |
| 94 | 2,6-Di-Cl | CH$_2$ | COOC$_8$H$_{17}$ |
| 95 | 2,6-Di-Cl | CH$_2$ | COOCH$_2$—CH$_2$—OCH$_3$ |
| 96 | 2,6-Di-Cl | CH$_2$ | COONa |
| 97 | 2-Cl, 4-F | CH$_2$ | COOH |
| 98 | 2-Cl, 4-F | CH$_2$ | COOCH$_3$ |
| 99 | 2-Cl, 4-F | CH$_2$ | COOC$_4$H$_9$ |
| 100 | 2-Cl, 4-Br | CH$_2$ | COOH |
| 101 | 2-Cl, 4-Br | CH$_2$ | COOC$_3$H$_7$ |
| 102 | 2-Cl, 4-CF$_3$ | CH$_2$ | COOH |
| 103 | 2-Cl, 4-CF$_3$ | CH$_2$ | COOC$_2$H$_5$ |
| 104 | 2-Cl, 4-CF$_3$ | CH$_2$ | COOC$_4$H$_9$ |
| 105 | 2-Cl, 4-CF$_3$ | CH$_2$ | COOC$_8$H$_{17}$ |
| 106 | 2-Cl, 4-CF$_3$ | CH$_2$ | COSC$_2$H$_5$ |
| 107 | 2-CH$_3$, 4-Cl | CH$_2$ | COOH |
| 108 | 2-CH$_3$, 4-Cl | CH$_2$ | COOCH$_3$ |
| 109 | 2-CH$_3$, 4-Cl | CH$_2$ | COOC$_4$H$_9$ |
| 110 | 2,4-Di-Cl, 6-CH$_3$ | CH$_2$ | COOH |
| 111 | 2,4-Di-Cl, 6-CH$_3$ | CH$_2$ | COOCH$_3$ |

TABLE I-continued

| Example | R¹³ | A | Z |
|---|---|---|---|
| 112 | 2,4-Di-Cl, 6-CH₃ | CH₂ | COOC₂H₅ |
| 113 | 2,3-Di-Cl, 4-NO₂ | CH₂ | COOH |
| 114 | 2,4-Di-CH₃ | CH₂ | COOH |
| 115 | 2,4-Di-Cl | —CH(CH₃)— | COOH |
| 116 | 2,4-Di-Cl | —CH(CH₃)— | COOCH₃ |
| 117 | 2,4-Di-Cl | —CH(CH₃)— | COOC₈H₁₇ |
| 118 | 2,4-Di-Cl | —CH(CH₃)— | COOCH₂—CH₂—OC₄H₉ |
| 119 | 2,4-Di-Cl | —CH(CH₃)— | COSCH₂CH₃ |
| 120 | 3,4-Di-Cl | —CH(CH₃)— | COOH |
| 121 | 3,4-Di-Cl | —CH(CH₃)— | COOCH₃ |
| 122 | 3,4-Di-Cl | —CH(CH₃)— | COOC₄H₉(n) |
| 123 | 3,4-Di-Cl | —CH(CH₃)— | COOCH₂CH₂—CH(OCH₃)—CH₃ |
| 124 | 3,4-Di-Cl | —CH(CH₃)— | COOCH₂—CH=CH₂ |
| 125 | 2,3-Di-Cl | CH(CH₃) | COOH |
| 126 | 2,3-Di-Cl | CH(CH₃) | COOC₆H₁₃ |
| 127 | 2,6-Di-Cl | CH(CH₃) | COOH |
| 128 | 2,6-Di-Cl | CH(CH₃) | COOC₂H₅ |
| 129 | 3,5-Di-Cl | CH(CH₃) | COOH |
| 130 | 3,5-Di-Cl | CH(CH₃) | COOC₃H₇ |
| 131 | 3,5-Di-Cl | CH(CH₃) | COOC₈H₁₇ |
| 132 | 3,5-Di-Cl | CH(CH₃) | COS—CH₂—COOC₄H₉ |
| 133 | 3,5-Di-Cl | CH(CH₃) | C(=O)—NH₂ |

TABLE I-continued

| Example | R¹³ | A | Z |
|---|---|---|---|
| 134 | 3,5-Di-Cl | CH(CH₃) | $\overset{\text{O}}{\underset{\|}{\text{C}}}-\text{NHC}_3\text{H}_7(\text{i})$ |
| 135 | 3,4-Di-Cl | CH₂ | CH₂OH |
| 136 | 3,4-Di-Cl | CH₂ | CH₂—O—C(=O)—CH₃ |
| 137 | 2,4-Di-Cl | CH₂ | CH₂OH |
| 138 | 2,4-Di-Cl | CH₂ | CH₂—O—C(=O)—CH₂—CH₃ |
| 139 | 3,5-Di-Cl | CH₂ | CH₂OH |
| 140 | 3,4-Di-Cl | CH(CH₃) | CH₂OH |
| 141 | 2,4-Di-Cl | CH(CH₃) | CH₂OH |
| 142 | 2-Cl, 4-F | CH(CH₃) | CH₂OH |
| 143 | 2-CH₃, 4-Cl | CH(CH₃) | CH₂OH |
| 144 | 2-Cl, 4-CF₃ | CH(CH₃) | CH₂OH |
| 145 | 2-Cl, 4-CF₃ | CH₂ | CH₂OH |
| 146 | 3,4-Di-Cl | CH₂ | CH₂—O—Benzyl |
| 147 | 3,4-Di-Cl | CH(CH₃) | CH₂—O—CO—NH—C₆H₄—Cl |
| 148 | 2,4-Di-Cl | CH₂ | CH(OC₂H₅)₂ |
| 149 | 2,4-Di-Cl | CH₂ | CH(OCH₃)₂ |
| 150 | 2,4-Di-Cl | CH₂ | 1,3-dioxolan-2-yl |
| 151 | 3,4-Di-Cl | CH₂ | 1,3-dioxan-2-yl |
| 152 | 3,4-Di-Cl | CH₂ | CH(OC₂H₅)₂ |
| 153 | 3,5-Di-Cl | CH₂ | CH(OC₂H₅)₂ |
| 154 | 3,4-Di-Cl | CH₂ | 4-(chloromethyl)-1,3-dioxolan-2-yl |
| 155 | 4-Cl | CH₂ | oxazolin-2-yl |

TABLE I-continued

| Example | $R^{13}$ | A | Z |
|---------|----------|-----|---|
| 156 | 3,4-Di-Cl | CH$_2$ | oxazoline ring |
| 157 | 4-Cl | CH$_2$ | 5-methyl oxazoline |
| 158 | 3,4-Di-Cl | CH$_2$ | 5-methyl oxazoline |
| 159 | 2-Cl—4-Br | CH$_2$ | 5-methyl oxazoline |
| 160 | 4-Cl | CH$_2$ | 4-ethyl oxazoline (C$_2$H$_5$) |
| 161 | 3,4-Di-Cl | CH$_2$ | 4,4-dimethyl oxazoline |
| 162 | 4-Cl | CH$_2$ | 4,4-dimethyl oxazoline |
| 163 | 4-Cl | CH$_2$ | 6-membered oxazine ring |
| 164 | 2,5-Di-Cl | CH$_2$ | COOH |
| 165 | 3-Cl | CH$_2$ | COOH |
| 166 | 2,4-Di-Cl | CH$_2$ | COOCH$_2$C≡CH |
| 167 | 2,4-Di-Cl | CH$_2$ | CONH$_2$ |
| 168 | 2,4-Di-Cl | CH$_2$ | CONHOH |
| 169 | 2,4-Di-Cl | CH(CH$_3$) | COOH$_2$CH$_2$—N(2,6-dimethylmorpholine) |
| 170 | 2,4-Di-Cl | CH(CH$_3$) | COOCH$_2$CH$_2$—SCN |
| 171 | 2,4-Di-Cl | CH(CH$_3$) | CONH$_2$ |

TABLE I-continued

| Example | R¹³ | A | Z |
|---|---|---|---|
| 172 | 3,4-Di-Cl | CH₂ | COO-(C₆H₃)(Cl)(Cl) (2,6-dichlorophenyl ester) |
| 173 | 3,4-Di-Cl | CH(CH₃) | COOCH₂C≡CH |
| 174 | H | CH(CH₃) | CONCS |
| 175 | 2,6-Di-Cl | CH₂ | CONCS |
| 175a | 3,5-Di-Cl | CH₂ | CONH₂ |

Naphthalene structure with R¹³ on one ring and O—A—Z substituent:

| Example | R¹³ | A | Z |
|---|---|---|---|
| 176 | 4-Cl | CH₂ | COOH |
| 177 | 4-Cl | CH₂ | COOCH₃ |
| 178 | 4-Cl | CH₂ | COOC₄H₉(n) |
| 179 | 2,4-Di-Cl | CH₂ | COOH |
| 180 | 2,4-Di-Cl | CH₂ | COOC₂H₅ |
| 181 | 2,4-Di-Cl | CH₂ | COOC₈H₁₇ |
| 182 | 2,4-Di-Cl | CH₂ | CONH₂ |
| 183 | 2,4-Di-Cl | CH₂ | CONHC₄H₉(n) |
| 184 | H | CH₂ | COOCH₃ |
| 185 | H | CH₂ | COSC₂H₅ |
| 186 | H | CH₂ | COOH |
| 187 | Cl | CH₂ | COONa |

Naphthalene structure with O—A—Z and R¹³ substituents:

| Example | R¹³ | A | Z |
|---|---|---|---|
| 188 | H | CH₂ | COOH |
| 189 | H | CH₂ | COOC₄H₉(n) |
| 190 | H | CH₂ | COOCH₃ |
| 191 | H | CH₂ | COSC₂H₅ |

The compounds of the general formula I are distinguished by the fact that they are applied in subtoxic concentrations in conjunction with herbicides and are then capable of antagonising, ie. of eliminating completely, the harmful side effects of the latter, without impairing their herbicidal effectiveness.

As a result of this it is possible to increase quite considerably the field of use of conventional plant treatment agents. The present invention also relates, therefore, to a process for the protection of crop plants against phytotoxic side effects of plant treatment agents, in particular herbicides, which comprises treating the plants, parts of plants of fertile soils for plants with a compound of the formula I before, after or at the same time as the plant protection agent.

Examples of herbicides in which the phytotoxic side effects can be reduced by means of compounds of the formula I are substituted phenoxycarboxylic, naphthoxycarboxylic and phenoxyphenoxycarboxylic acid derivatives and hetero-aryloxyphenoxycarboxylic acid derivatives, such as quinolyloxy-, quinoxalyloxy-, pyridyloxy-, benzoxazolyloxy- or benzthiazolyloxy-phenoxycarboxylic acid esters, and also dimedone oxime derivatives. Phenoxycarboxylic and hetero-aryloxyphenoxycarboxylic acid esters are preferred in this respect.

Without the intention that a limitation should arise thereby, herbicides from the following classes may be mentioned as examples:

(A) Herbicides of the type of ($C_1$–$C_4$)-alkyl, ($C_2$–$C_4$)-alkenyl and ($C_3$–$C_4$)-alkynyl-phenoxyphenoxycarboxylates and hetero-aryloxyphenoxycarboxylates, such as 1. methyl 2-(4-(2,4-dichlorophenoxy)-phenoxy)-propionate,
2. methyl 2-(4-(4-bromo-2-chlorophenoxy)-phenoxy)-propionate,
3. methyl 2-(4-(4-trifluoromethylphenoxy)-phenoxy)-propionate,
4. methyl 2-(4-(2-chloro-4-trifluoromethylphenoxy)-phenoxy)-propionate,
5. methyl 2-(4-(2,4-dichlorobenzyl)-phenoxy)-propionate,
6. ethyl 4-(4-(4-trifluoromethylphenoxy)-phenoxy)-pent-2-enoate,
7. ethyl 2-(4-(3,5-dichloropyridyl-2-oxy)-phenoxy)-propionate,
8. ethyl 2-(4-(3,5-dichloropyridyl-2-oxy)-phenoxy)-propionate,
9. ethyl 2-(4-(6-chlorobenzoxazolyl-2-oxy)-phenoxy)-propionate, 10. ethyl 2-(4-(6-chlorobenzthiazolyl-B 2-oxy)-phenoxy)-propionate,
11. methyl 2-(4-(3-chloro-5-trifluoromethyl-2-pyridyloxy)-phenoxy)-propionate,
12. butyl 2-(4-(5-trifluoromethyl-2-pyridyloxy)-phenoxy)-propionate,
13. ethyl 2-(4-(6-chloro-2-quinoxalinyloxy)-phenoxy)-propionate.

(B) Dimedone derivatives, such as:
1. 2-(N-ethoxybutyrimidoyl)-5-(2-ethylthiopropyl)-3-hydroxy-2-cyclohexen-1-one,
2. 2-(N-ethoxybutyrimidoyl)-5-(2-phenylthiopropyl)-3-hydroxy-2-cyclohexen-1-one or
3. 2-(1-allyloxyiminobutyl)-4-methoxycarbonyl-5,5-dimethyl-3-oxocyclohexenol.

The antidote:herbicide ratio can vary within wide limits between 0.1 and 5 parts of antidoe to 1 part of herbicide. The amounts of herbicide and antidote which are optimum in a particular case depend on the type of herbicide or antidote used and on the nature of the crop of plants to be treated, and can be determined from case to case by appropriate tests.

Main fields of use for the application of the safeners are, above all, cereal crops (wheat, rye, barley or oats), rice, maize and sorghum but also cotton, sugar beet, sugar cane and soya beans.

Depending on their properties, the safeners can be used to pretreat the seed of the crop plant (seed dressing) or can be introduced into the seed furrows before sowing or can be used, together with the herbicide, before or after the emergence of the plants. Pre-emergence treatment includes both the treatment of the cultivated area before sowing and the treatment of cultivated areas which have been sown, but are not yet covered with vegetation.

In principle, the antidote can be applied before, after or at the same time as a herbicide, but simultaneous application in the form of tank mixtures or, if appropriate, finished formulations is preferred.

For application, the compounds of the formula I are made up with customary formulation auxiliaries to give dusting agents, wettable powders, dispersions, emulsion concentrates, granules or microgranules which contain the active compound in concentrations of 2–80% and are either applied as such (dusting agents or pellets) or are dissolved or dispersed in a solvent (water) before application.

Wettable powders are preparations which are uniformly dispersible in water and which, in addition to the active compound and apart, if appropriate, from a diluent or inert substance, also contain wetting agents, for example polyoxethylated alkylphenols, polyoxethylated fatty alcohols, alkylsulfonates or alkylphenylsulfonates, and dipsersing agents, for example sodium ligninsulfonate, sodium 2,2'-dinaphthylmethane-6,6'-disulfonate, sodium dibutylnaphthalenesufonate or sodium oleoylmethyltauride. Preparation is effected in a customary manner, for example by grinding and mixing the components.

Emulsifiable concentrates can be prepared, for example, by dissolving the active compound in an inert organic solvent, for example butanol, cyclohexanone, dimethylformamide, xylene or higher-boiling aromatic compounds or hydrocarbons, with the addition of one or more emulsifiers. In the case of liquid active compounds, the solvent component can also be omitted wholly or partly. The following are examples of emulsifiers which can be used: calcium alkylarylsulfonates, such as Ca dodecylbenzenesulfonate, or nonionic emulsifiers, such as polyglycol fatty acid esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxethylene sorbitan fatty acid esters or esters of polyoxethylene sorbitol.

Dusting agents can be obtained by grinding the active compound with finely divided, solid substances, for example talc, natural clays, such as kaolin, bentonite or pyrophillite, or diatomaceous earth.

Granules can be prepared either by atomizing the active compound onto adsorbent, granulated inert material or by applying concentrations of active compounds to the surface of carriers, such as sand or kaolinite, or granulated inert material by means of binders, for example polyvinyl alcohol, sodium polyacrylate or mineral oils. Suitable active compounds can also be granulated in the manner customary for the production of fertilizer granules, if desired as a mixture with fertilizers.

In wettable powders, the concentration of active compound is, for example, about 10 to 90% by weight, the remainder up to 100% by weight being composed of customary formulation ingredients. In the case of emulsifiable concentrates, the concentration of active compound can be about 10 to 80% by weight. Formulations in the form of dusts contain im most cases 5 to 20% by weight of active compound, while atomizable solutions contain about 2 to 20% by weight. In the case of granules, the content of active compound depends partly on whether the active compound is in a liquid or solid form and on the granulating auxiliaries, fillers etc. which are used.

In addition, the active compound formulations mentioned optionally contain the tackifiers, wetting agents, dispersing agents, emulsifiers, penetration agents, solvents, fillers or carriers which are customary in a particular case.

For application, the concentrates, present in a commercial form, are optionally diluted in a customary manner, for example by means of water in the case of wettable powders, emulsifiable concentrates and dispersions and, in part, also in the case of microgranules. Preparations in the form of dusts and granules and also atomizable solutions are usually not diluted further with further inert substances before application.

A. Formulation examples a. A dusting agent is obtained by mixing 10 parts by weight of safener and 90 parts by weight of talc or an inert substance and comminuting the mixture in a beater mill.

b. A wettable powder which is readily dispersible in water is obtained by mixing 25 parts by weight of safener, 64 parts by weight of kaolin-containing quartz as an inert substance, 10 parts by weight of potassium ligninsulfonate and 1 part by weight of sodium oleoylmethyltauride as a wetting and dispersing agent, and grinding the mixture in a pin disk mill.

c. A dispersion concentrate which is readily dispersible in water is obtained by mixing 20 parts by weight of safener with 6 parts by weight of an alkylphenol polyglycol ether (Triton X 207), 3 parts by weight of isotridecanol polyglycol ether (8 EO) and 71 parts by weight of paraffinic mineral oil (boiling range, for example, approx. 255° to over 377° C.), and grinding the mixture in a ball mill to a fineness of less than 5 microns.

d. An emulsifiable concentrate is obtained from 15 parts by weight of safener, 75 parts by weight of cyclohexanone as solvent and 10 parts by weight of oxethylated nonylphenol as emulsifier.

BIOLOGICAL EXAMPLES

EXAMPLE 1

Wheat and wild oats (Avena fatua) were sown and cultivated under greenhouse conditions to the 4-leaf stage. A number of antidotes according to Table I and the herbicide A9 were then sprayed onto the test plants in various dosages. After waiting a further period of 4 weeks in the greenhouse, the plants were investigated to check any kind of inhibition or damage in comparison with test plants not treated with antidote. The results show that the antidotes greatly reduce the harmful herbicidal effects on wheat, without impairing the herbicidal effectiveness against the gramineous weeds Avena and Alopecurus:

TABLE II

| | Antidote action in soft wheat | | |
|---|---|---|---|
| Compound (Example) | Dosage kg of active ingredient/ hectare | Herbicidal action, % TA | AVF |
| A9 | 2 | 85 | — |
| | 0,3 | — | 90 |
| A9 + 151 | 2 + 1 | 35 | — |
| | 0,3 + 1 | — | 95 |
| A9 + 152 | 2 + 1 | 60 | — |
| | 0,3 + 1 | — | 90 |
| A9 + 160 | 2 + 1 | 25 | — |
| | 0,3 + 1 | — | 95 |
| A9 + 162 | 2 + 1 | 10 | — |
| | 0,3 + 1 | — | 85 |
| A9 + 184 | 2 + 1 | 32 | — |
| A9 + 188 | 2 + 1 | 28 | — |
| A9 + 190 | 2 + 1 | 38 | — |
| A9 + 92 | 2 + 1 | 25 | — |
| A9 + 67 | 2 + 1 | 20 | — |
| A9 + 164 | 2 + 1 | 40 | — |
| A9 + 31 | 2 + 1 | 28 | — |
| | 0,3 + 1 | — | 90 |
| A9 + 165 | 2 + 1 | 25 | — |
| | 0,3 + 1 | — | 90 |
| A9 + 70 | 2 + 1 | 23 | — |
| | 0,3 + 1 | — | 88 |
| A9 + 120 | 2 + 1 | 55 | — |
| A9 + 170 | 2 + 1 | 50 | — |
| A9 + 73 | 2 + 1 | 20 | — |
| | 0,3 + 1 | — | 90 |
| A9 + 32 | 2 + 1 | 13 | — |
| | 0,3 + 1 | — | 92 |
| A9 + 173 | 2 + 1 | 18 | — |
| A9 + 172 | 2 + 1 | 20 | — |
| A9 + 78 | 2 + 1 | 22 | — |
| | 0,3 + 1 | — | — |
| A9 + 174 | 2 + 1 | 22 | — |
| A9 + 175 | 2 + 1 | 25 | — |
| A9 + 175a | 2 + 1 | 30 | — |
| A9 + 84 | 2 + 1 | 50 | — |

TABLE II-continued

| | Antidote action in soft wheat | | |
|---|---|---|---|
| Compound (Example) | Dosage kg of active ingredient/ hectare | Herbicidal action, % TA | AVF |
| — | — | — | — |

Abbreviations:
A9 = Fenoxaprop ethyl.
TA = Triticum aestivum.
AVF = Avena fatua

EXAMPLE 2

In a further test, the antidote action of a number of compounds from Table I was tested in the treatment of barley with the herbicide A1. The cultivation and treatment of the test plants was carried out as described in Example 1. Here too, a considerable reduction was observed in the harmful action of A1 on useful plants:

TABLE III

| | Antidote action in barley | |
|---|---|---|
| Product | Dosage kg of active ingredient/ hectare | Herbicidal action, % HD |
| A1 | 2,5 | 80 |
| A1 + 159 | 2,5 + 2,5 | 45 |
| A1 + 116 | 2,5 + 2,5 | 30 |
| A1 + 169 | 2,5 + 2,5 | 20 |
| A1 + 166 | 2,5 + 2,5 | 40 |
| A1 + 167 | 2,5 + 2,5 | 50 |
| A1 + 171 | 2,5 + 2,5 | 30 |

Abbreviations:
A1 = Diclofop methyl
HD = Hordeum distichum

EXAMPLE 3

The antidote action of compounds from Table I in the treatment of maize with A1 was investigated in the same way. The cultivation and treatment of the plants was as in Example 1.

TABLE IV

| | Antidote action in maize (Zea mays) | |
|---|---|---|
| Product | Dosage kg of active ingredient/ hectare | Herbicidal action, % |
| A1 | 0,4 | 95 |
| A1 + 135 | 0,4 + 2,5 | 30 |
| A1 + 140 | 0,4 + 2,5 | 30 |
| A1 + 146 | 0,4 + 2,5 | 40 |
| A1 + 147 | 0,4 + 2,5 | 42 |
| A1 + 155 | 0,4 + 2,5 | 20 |
| A1 + 157 | 0,4 + 2,5 | 30 |
| A1 + 156 | 0,4 + 2,5 | 30 |
| A1 + 158 | 0,4 + 2,5 | 30 |
| A1 + 161 | 0,4 + 2,5 | 40 |
| A1 + 163 | 0,4 + 2,5 | 30 |
| A1 + 185 | 0,4 + 2,5 | 20 |
| A1 + 191 | 0,4 + 2,5 | 30 |
| A1 + 122 | 0,4 + 2,5 | 40 |
| A1 + 168 | 0,4 + 2,5 | 30 |

EXAMPLE 4

Weeds and cereals were grown in a greenhouse and treated in the 4–6 leaf stage with the antidote of example 107 and the herbicide A9 alone and in combination at various concentrations, 4 weeks later the results were assessed visually. They are shown in Table V.

As is evident from the Table, A9 alone caused visible damages in wheat (triticum aestivum) at concentrations necessary to obtain efficient control of wild oats (avena fatua) and blackgrass (alopecurus myosuroides). Combinations of A9 with 107 (which alone is inactive against the two weeds) surprisingly showed considerably better crop tolerance against wheat at effective weed control levels. The addition of 107 thus permits the selective use of A9 in wheat.

The combination furthermore has a synergistic effect against e.g. wild mustard (sinapis arvensis) as compared with the single components. The synergism results from a comparison of the total "additive" activity calculated from the activities of the single components, with the actual "experimental" activity. The additive activity is calculated according to the Colbyformula (S. R. Colby, "Weeds" 15, pages 20–22 (1967) which reads $$E = X + Y - (X.Y/100)$$

in which

X = % damage caused by application of x kg/ha of A9

Y = % damage caused by application of y kg/ha of 107

E = expected damage in % caused by application of (x+y) kg/ha of A9+107

If the experimental activity is greater than the calculated activity, synergism is present. The results in Table V show such synergism, as is evident from the figures in brackets (calculated activity) as compared with the figures showing actual activity.

TABLE V

| | | Herbicidal activity (damage) and selectivity in post-emergence application (in percent) | | | |
|---|---|---|---|---|---|
| Compound | Dose g AS/ha | Triticum aestivum | Avena fatua | Alopecurus myosuroides | Sinapis arvensis |
| A9 | 50 | 0 | 63 | 60 | 0 |
| | 100 | 15 | 90 | 80 | 10 |
| | 150 | 25 | 100 | 92 | 15 |
| | 200 | 33 | 100 | 100 | 25 |
| | 300 | 60 | — | — | — |
| 107 | 25 | 0 | 0 | 0 | 30 |
| | 50 | 0 | 0 | 0 | 45 |
| | 100 | 0 | 0 | 0 | 58 |
| | 150 | 0 | 0 | 0 | 65 |
| | 200 | 0 | 0 | 0 | 76 |
| | 300 | 0 | 0 | 0 | 84 |
| | 400 | 0 | 0 | 0 | — |
| | 600 | 0 | 0 | 0 | — |
| A9 + 107 (1:0,5) | 50 + 25 | 0 | 78 (63) | 70 (60) | 69 (30) |
| | 100 + 50 | 0 | 95 (90) | 85 (80) | 82 (51) |
| | 150 + 75 | 0 | 100 | 98 (92) | 85 — |
| | 200 + 100 | 0 | 100 | 100 | 95 (69) |
| | 300 + 150 | 15 | — | — | — |
| A9 + 107 (1:1) | 50 + 50 | 0 | 76 (63) | 75 (60) | 72 (45) |
| | 100 + 100 | 0 | 92 (90) | 85 (80) | 86 (63) |
| | 150 + 150 | 0 | 100 | 99 (92) | 93 (71) |
| | 200 + 200 | 0 | 100 | 100 | 98 (82) |
| | 300 + 300 | 10 | — | — | — |
| A9 + 107 (1:2) | 50 + 100 | 0 | 80 (63) | 75 (60) | 86 (58) |
| | 100 + 200 | 0 | 95 (90) | 86 (80) | 89 (79) |
| | 150 + 300 | 0 | 100 | 98 (92) | 93 (87) |
| | 200 + 400 | 0 | 100 | 100 | 99 |
| | 300 + 600 | 0 | — | — | — |

We claim:

1. A method for protecting wheat against the phytotoxic side effects of a herbicidally-effective amount of ethyl 2-[4-(6-chlorobenzoxazol-2-oxy)-phenoxy]propionate applied to said wheat as a herbicide, which method comprises applying to said plants, to parts of said plants, or to fertile soil for plants which are to be treated, at the same time as herbicide, an antidotally-effective amount of a safener which is a compound of the formula Ar—O—A—Z wherein Ar is phenyl mono- or di-substituted by the same or different halogen atoms or by $(C_1-C_4)$-alkyl;

A is —$CH_2$— or —$CH(CH_3)$—;

Z is —COOR'; and

R' is hydrogen, linear or branched $(C_1-C_{12})$-alkyl, or a cation of an organic or inorganic base.

2. A method as in claim 1 wherein the ratio by weight of said safener to said herbicide is from 1:2 to 5:1.

3. A method as in claim 1 wherein said safener is 3,4-dichlorophenoxy acetic acid.

* * * * *